US005885908A

United States Patent [19]
Jaeger et al.

[11] Patent Number: 5,885,908
[45] Date of Patent: Mar. 23, 1999

[54] ANISOTROPIC ELASTIC FILMS

[75] Inventors: Jobst Tilman Jaeger, Kaarst, Germany; Alan J. Sipmen, North Oaks, Minn.

[73] Assignee: Minnesota Mining and Manufacturing Co., St. Paul, Minn.

[21] Appl. No.: 720,794

[22] Filed: Oct. 4, 1996

[51] Int. Cl.⁶ .................................................. B29C 63/00
[52] U.S. Cl. ................................. 442/59; 442/1; 442/50; 442/51; 442/54; 442/57; 442/58; 442/60; 442/62; 442/63; 442/76; 442/77; 442/85; 442/152; 442/155; 442/156; 442/164; 442/327; 442/328; 442/329; 442/361; 442/381; 442/400; 442/414; 442/415; 442/416
[58] Field of Search ..................................... 442/1, 50, 51, 442/54, 57, 58, 59, 60, 62, 63, 76, 77, 85, 152, 155, 156, 164, 327, 328, 329, 361, 381, 400, 414, 415, 416

[56] References Cited

U.S. PATENT DOCUMENTS

| | | | |
|---|---|---|---|
| 3,819,404 | 6/1974 | Scholes et al. | 117/106 R |
| 3,912,565 | 10/1975 | Koch et al. | 156/85 |
| 3,949,128 | 4/1976 | Ostermeier | 428/152 |
| 4,413,623 | 11/1983 | Pieniak | 604/365 |
| 4,525,407 | 6/1985 | Ness | 428/138 |
| 4,606,964 | 8/1986 | Wideman | 428/152 |
| 4,720,515 | 1/1988 | Iji et al. | 523/435 |
| 4,965,122 | 10/1990 | Morman | 428/225 |
| 4,981,747 | 1/1991 | Morman | 428/196 |
| 5,167,897 | 12/1992 | Weber et al. | 264/288.8 |
| 5,226,992 | 7/1993 | Morman | 156/62.4 |
| 5,344,691 | 9/1994 | Hanschen et al. | 428/152 |
| 5,354,597 | 10/1994 | Capik et al. | 428/152 |
| 5,366,793 | 11/1994 | Fitts, Jr. et al. | 428/198 |
| 5,385,775 | 1/1995 | Wright | 428/284 |
| 5,462,708 | 10/1995 | Swenson et al. | 264/174.11 |
| 5,501,675 | 3/1996 | Erskine | 604/263 |
| 5,501,679 | 3/1996 | Krueger et al. | 604/393 |
| 5,514,470 | 5/1996 | Haffner et al. | 428/246 |
| 5,527,304 | 6/1996 | Buell et al. | 604/385.2 |
| 5,539,056 | 7/1996 | Yang et al. | 525/240 |

FOREIGN PATENT DOCUMENTS

| | | | |
|---|---|---|---|
| 0114964A1 | 8/1984 | European Pat. Off. | C08L 23/04 |
| 693585 A2 | 1/1996 | European Pat. Off. | D04H 1/54 |
| 0707106 A1 | 4/1996 | European Pat. Off. | D04H 13/00 |
| 59-155478 | 9/1984 | Japan | C09J 7/00 |
| 7-213554 | 8/1995 | Japan | A61F 13/15 |
| 7-286051 | 10/1995 | Japan | C08J 5/18 |
| 8-58038 | 3/1996 | Japan | B32B 27/30 |
| 8-59903 | 3/1996 | Japan | C08L 23/02 |
| 2178433 | 2/1987 | United Kingdom | C08L 23/02 |
| 94/18263 | 8/1994 | WIPO | C08J 5/18 |
| 95/33006 | 12/1995 | WIPO | C08L 53/02 |
| WO 95/34264 | 12/1995 | WIPO | A61F 13/15 |
| WO 96/10481 | 4/1996 | WIPO | B32B 5/04 |

OTHER PUBLICATIONS

In situ production of polyethylene fibres from polymer blends by F. Ehtaiatkar et al., *Journal of Materials Science* 24 pp. 2808–2814 (1989).
Polymer Blends and Alloys by M. J. Folkes et al., Blackie Academic & Professional pp. 228–255.
The Effects of Blending Small Amounts of Homopolystyrene by L. S. Flosenzier, Polymer Engineering and Science, vol. 30, No. 1, pp. 50–58 (1990).
Microfiber Formation: Immiscible Polymer Blends Involvin Thermoplastic Poly(vinyl alcohol) as an Extractable Matrix by L. M. Robeson et al., Journal of Applied Polymer Science, vol. 52, pp. 1837–1846 (1994).
Deformation of melts of mixtures of incompatible polymers in a uniform shear field and the process of their fibrillation by V. E. Dreval, Rheol. Acta 22, pp. 102–107 (1983).
S–B–S Block Copolymer–Polystyrene Blends: 1. Morphology and Swelling Properties by M.J. Folkes and P.W. Reip, *Department of Materials Technology, Brunel University, Uxbridge, Middlesex,* UB8 3PH, UK (1985).

*Primary Examiner*—Ardin H. Marschel
*Attorney, Agent, or Firm*—Gary L. Griswold; Robert W. Sprague; William J. Bond

[57] ABSTRACT

An anisotropic elastic web, particularly an anisotropic elastic film layer having a machine direction and a cross direction and having a thickness of from 20 to 300 microns formed of an extruded blend of a block copolymer elastomer portion and a polyolefin polymer portion blended in a ratio of from 10:1 to 0.4:1, respectively. The elastomer portion generally is a block copolymer elastomer formed of A blocks and B blocks, the A blocks are formed predominately of monoalkenyl arene and the B blocks are formed predominately of conjugated diene. The polyolefin portion is comprised predominately of an inelastic fiber forming polyolefin polymer, copolymer or blend. The anisotropic film layer has a F10 force Ratio (MD to CD) of at least 1.5. This anisotropic elastic web is usable in a variety of garment applications where an elastic is supplied in roll form and requires strength in a machine direction and elastic properties in a cross direction.

28 Claims, No Drawings

ANISOTROPIC ELASTIC FILMS

BACKGROUND AND FIELD OF THE INVENTION

The invention concerns elastic film materials and laminates containing elastic film materials.

Thin elastic film materials, nonwovens and other like web materials are used with increasing frequency in the disposable or personal use garment product area, garment meaning a product used on, or in association with, a body (human or animal). Specifically, such uses include disposable diapers, training pants, incontinence articles, sanitary napkins, bandages, surgical drapes and gowns, medical nonwovens, face masks, sport wraps and the like. Generally, these elastomeric materials are formed of conventional elastomers which generally exhibit elastic properties in substantially all directions, particularly if in the form of an elastic film. However, for some specific applications, it is desirable to have materials which are primarily elastic in only a single direction, i.e., anisotropic elastic materials. A large number of patent applications and patents have been directed towards this problem, providing a wide variety of solutions. The most common approach in the art has been to laminate an elastic web material to a second web material that is easily stretched in one direction but not in the transverse direction. PCT application No. WO 96/10481 discusses a version of this approach stating that a common practice has been to produce a so-called "stretch-bonded laminate". With these stretch-bonded laminates, an elastic film or nonwoven, or like elastic web, is elongated in one direction. While elongated, the elastic web is either continuously or point-bonded to an inelastic web material. Afterwards, tension is released and the elastic web is allowed to recover in the direction opposite to its elongation. The attached inelastic web material then puckers making the stretch-bonded laminate readily extensible in the direction of the elastic web's elongation but not in the transverse direction. The laminate can then be restretched up to the point of previous elongation of the elastic web. However, this puckering is indicated as undesirable for some applications. In order to overcome the puckering problem, the WO 96/10481 application proposes using an inelastic nonwoven web material with a large number of substantially parallel slits. This slit nonwoven web material is then attached to an untensioned elastic web material. When the laminate is then stretched in a direction perpendicular to the direction of the slits the laminate stretches and recovers without the formation of puckers or gathers in the inelastic nonwoven web.

Some patent documents which discuss or are directed at the prior art methods disclosed in the above PCT application include European Patent Application No. 693585 A2 and U.S. Pat. Nos. 4,413,623; 4,606,964 and 4,720,515 all of which stretch an elastic web material and then point bond, or otherwise bond the stretched elastic web to a relatively inelastic web material, which inelastic web material subsequently gathers when the tensioned elastic web is allowed to recover. In a variation of this, U.S. Pat. No. 4,525,407 joins elastic and inelastic web materials while the elastic web is untensioned. The laminate is point bonded and then stretched under tension strong enough to cause the inelastic web material to permanently deform, which deformed inelastic material then puckers or gathers upon recovery of the elastic material. A method similar to this is disclosed in, e.g., U.S. Pat. Nos. 5,527,304 and 5,167,897. The materials formed in these patents have been termed "zero strain" elastic materials in that the inelastic and elastic web materials are joined without either being under strain. The one or more inelastic web materials and the elastic web materials are then subject to particular forms of incremental stretching between meshed corrugating rolls. Other randomly gathered materials can also be produced using heat shrinkable elastics such as disclosed in U.S. Pat. Nos. 3,819,404 and 3,912,565.

Also disclosed is a nonwoven inelastic web corrugated between geared teeth or corrugating rolls. While the inelastic web is corrugated, it is bonded to an elastic web material by extrusion lamination or adhesive lamination such as disclosed, respectively, in PCT Application No. WO 95/34264 and Japanese Kokai No. HEI 7-213554. These laminated materials have relatively large, uniform and regular gathers as compared to the other methods described above. These materials also have relative uniform elastomeric properties and are aesthetically pleasing. However, these elastic laminates are generally very thick and as such can be unsuitable for certain types of uses requiring a flatter profile elastic material.

Anisotropic elastic materials having cross-directional elasticity are disclosed, for example, in U.S. Pat. Nos. 5,514,470; 4,965,122; 5,226,992; 4,981,747 and European Patent No. 707106. In these patents, there is used a "neckable" inelastic nonwoven web material. Suitable neckable nonwoven webs include spunbond, meltblown or bonded carded webs. The neckable nonwoven webs are stretched in a machine direction in a manner which causes the inelastic web materials to neck (i.e., decrease in width) in the cross direction. While the nonwoven web materials are necked in this manner they are joined to an elastic web such as a film or nonwoven, either continuously or in a point bonded manner. The resulting laminate material is generally inelastic in the machine direction while being substantially elastic in the cross direction up to the original cross dimensional width of the reversibly necked material.

An inelastic nonwoven web material exhibiting directional elastic-type properties is disclosed in U.S. Pat. No. 3,949,128. In this patent, a continuous filament nonwoven web, as would be produced by a spunbond process, is point bonded and then either stretched in the machine direction or microcreped in the machine direction and then subjected to heat setting. Depending on whether the heat set web material is stretched or microcreped, it exhibits a CD elastic-like property or MD elastic-like property, respectively.

U.S. Pat. No. 5,366,793 discloses an anisotropic elastomeric nonwoven fibrous web of meltblown elastomeric fibers. The anisotropic behavior is obtained by aligning the fibers with an airstream to produce a web with a higher peak load tension in the direction of fiber orientation.

In U.S. Pat. Nos. 5,344,691; 5,501,679 and 5,354,597 there is disclosed multilayered elastomeric films including those having an elastomeric central layer with one or two outer film layers of a relatively inelastic material. The multilayer films are coextruded so as to produce thin inelastic film layers and a relatively thick elastic film layer. These coextruded film materials are termed stretch activated elastic (SAE) and are substantially inelastic as formed but if stretched in one direction and allowed to recover will exhibit uniaxial elastic properties in the direction in which the laminate has been stretched and recovered. The materials which have been stretched uniaxially will exhibit substantially anisotropic elastic behavior. The anisotropic elastic behavior in these coextruded laminates can be accentuated as described in U.S. Pat. No. 5,462,708 by subjecting a uniaxially stretched laminate to a deactivating heat treatment, while in the stretched condition. The heat treatment is such that the elastic recovery force of the elastic material is allowed to dissipate without substantially affecting the orientation of the inelastic skin materials. The heat treated laminate material is then stretched in a second cross direction and allowed to recover as described above. The resulting material is exceedingly strong in the original stretch direction and elastic in the cross direction. Generally, these SAE materials are extremely advantageous where a low profile-type elastic web is required, which elastics can have either isotropic or anisotropic elastic properties as may be required.

An anisotropic, single-layer, film-type elastic is disclosed in Japanese Patent Kokai No. 5-186611, this patent discloses extrusion of a blend of an ABA block copolymer with polystyrene where the polymers are exemplified as blended at a ratio of from 50 to 99 percent block copolymer to 1 to 50 percent polystyrene. The resulting material produced exhibits anisotropic elastic behavior. Polypropylene is exemplified as not working to produce anisotropic behavior. Materials of the type disclosed in this Kokai have been found to have relatively low tear resistance and unless suitably treated with an antiblocking agent or the like tend to exhibit high blocking behavior.

There is a continuous need for further forms of anisotropic elastic webs suitable for use in a wide variety of potential applications which web materials are easy to manufacture, form readily into a roll and subsequently easily unwound without blocking, handled and converted into its final form for use on a limited-use garment and the like.

SUMMARY OF THE INVENTION

An anisotropic elastic web comprising an anisotropic elastic film layer having a machine direction and a cross direction and having a thickness of from about 20 to 300 microns is formed of an extruded blend of a block copolymer elastomer portion and a polyolefin polymer portion blended in a ratio of from generally 10:1 to 0.4:1, respectively. The elastomer portion comprises a block copolymer elastomer formed of A blocks and B blocks, the A blocks are formed predominately of monoalkenyl arene and the B blocks are formed predominately of conjugated diene and the polyolefin portion is comprised predominately of an inelastic polyolefin polymer, copolymer or blend. The anisotropic film layer has a F10 Ratio (MD to CD) of at least 1.5, preferably greater than 2.0. This anisotropic elastic film can be formed into a roll of film which can be unwound without blocking.

In a second embodiment the anisotropic elastic film can comprise a multilayer film of said anisotropic elastic film layer and at least one other polymer film layer. The other film layer is generally a relatively inelastic film layer compared to said elastic film layer and said film layers are coextruded.

Generally the anisotropic elastic web has an average tear strength of at least 20 g/25 $\mu$ and the permanent set of the anisotropic elastic film layer in the CD direction is less than about 80 percent when the film layer is stretched by 200 percent. The film is generally untensilized but can be tensilized in the machine direction for additional anisotropic properties.

DESCRIPTION OF THE PREFERRED EMBODIMENTS

The present invention relates to generally nonblocking thin anisotropic elastic films and elastic laminates using such films. The anisotropic elastic films are characterized by having a machine direction and a substantially perpendicular cross-direction. The elastic properties of the film are substantially anisotropic in that the films are substantially less elastic in a machine direction relative to a cross direction, i.e., the film, as formed, is substantially more elastic in the cross direction than in the machine direction, as defined herein.

Generally, in the cross direction, the invention film, as formed, when initially stretched by approximately 200 percent will recover and sustain a permanent set upon relaxation which is generally less than 80 percent and preferably less than 50 percent of the original length of the elastic film or film laminate. Although the machine direction may exhibit elastomeric properties, the force required for incremental elongation in the machine direction will be substantially higher than in the cross direction, at least at low levels of elongation of less than 5 to 10 percent.

The anisotropic elastic film of the invention is formed by extruding the film material from a blend of a block copolymer(s) elastomer portion with an olefinic relatively inelastic polymer material(s) portion. The invention anisotropic film generally demonstrates improved tear resistance relative to known anisotropic, single-layer, elastic films as are discussed in Japanese Patent Application Kokai No. 5-186611. However, this improved tear resistance can be obtained without substantial reduction in the anisotropic elastic properties of the film or significant reductions in overall elasticity of the invention film.

The block copolymer elastomers in the elastomer portion are generally formed of A and B blocks where the A block is formed predominately of monoalkenyl arenes, preferably styrenic moieties and most preferably styrene, having a block molecular weight distribution between 4,000 and 50,000. The B block(s) is formed predominately of conjugated dienes, and has an average molecular weight of from between about 5,000 to 500,000, which B block(s) monomers can be further hydrogenated or functionalized. The A and B blocks are conventionally configured in linear, radial or star configuration, among others, where the block copolymer contains at least one A block and one B block, but preferably contains multiple A and/or B blocks, which blocks may be the same or different. A preferred block copolymer of this type is a linear ABA block copolymer where the A blocks may be the same or different. Also preferred are other multi-block (block copolymers having more than three blocks) copolymers having predominately A terminal blocks. These preferred multi-block copolymers can also contain a certain proportion of AB diblock copolymer. However, generally the amount of AB diblock copolymer should be limited as it tends to form a more tacky elastomeric film having an increased tendency to block, unless in a laminate form. Generally, the amount of diblock is less than 50 percent, preferably less than 20 percent of the elastomer portion of the anisotropic elastic film. To a certain extent, minor proportions of other elastomers can be blended with the block copolymer elastomer(s) provided that they do not adversely affect the anisotropic elastomeric properties of the elastic film material as defined above. Other than polystyrene, the A blocks can be formed from alphamethyl styrene, t-butyl styrene and other predominately alkylated styrenes, as well as mixtures and copolymers thereof. The B block can generally be formed from isoprene, 1,3-butadiene or ethylene-butylene monomers, however, preferably is isoprene.

The inelastic polymer material portion blended with the block copolymer elastomer portion is generally predominately a fiber forming polyolefin, exemplary polyolefins include polypropylene, polyethylene, ethylene-propylene copolymers, impact copolymers, polypropylene copolymers, butene polymers and copolymers and blends thereof. The ratio of the elastomer portion to the polyolefin inelastic polymer portion is generally from 10:1 to 0.4:1, preferably 5:1 to 0.6:1. A minor portion of the inelastic polymer portion of the invention blend can include nonolefinic materials, generally from 0 to 20 percent, preferably 0 to 10 percent of the inelastic polymer portion provided that the additional nonolefinic materials are substantially incompatible with the block copolymer portion and are preferably similarly fiber forming or compatible with the polymer of the inelastic polymer material portion.

The overall thickness of the anisotropic elastic film formed is generally from 20 to 300 $\mu$, preferably 25 to 100 $\mu$. If the elastic material thickness is greater than 300 $\mu$ the material would be too difficult to elongate in the cross direction making it unsuitable for use in garments and the like for which the invention film material is designed. If the film thickness is less than 20 $\mu$, generally the elastic force provided by the invention film is insufficient. Generally the force required to stretch the film in the more elastic cross direction by 10 percent, as defined in the examples, is less than about 60 kg/cm$^2$, preferably less than 40 kg/cm$^2$ and most preferably less than 20 kg/cm$^2$. Further, the ratio (F10 Ratio) of this 10 percent force in the machine direction (MD) to the cross direction (CD) is generally greater than 1.5, preferably greater than 2.0, and most preferably greater than 2.5. This F10 force ratio is one measure of the anisotropic elastic behavior of the invention film.

The invention films can exhibit improved tear resistance when compared to the films formed of the elastomer portion only. Generally this is at least a 50 percent improvement, preferably a 100 percent improvement, ranging to up to a 10 fold improvement or more depending on the materials and their relative proportions. Generally this improvement is noted after the elastomer portion to polymer portion ratio is greater than 3 down to about 2. The tear resistance as defined in the examples is preferably at least 20 g/25 $\mu$ and most preferably at least 30 g/25 $\mu$. The non-blocking behavior is generally noted when the elastomer portion to polymer portion ratio is less than about 2.5:1.

Generally, the invention anisotropic film can be formed into a roll for subsequent use without substantial blocking or stretching of the elastic film in the machine direction when being unwound from the roll. Blocking in this invention refers to the relative tendency of the film or laminate to adhere to itself in roll form. If this self-adhesion is too high, the film will either not unwind or unwind with great difficulty and possibly damage the film. Generally, the unwind force for a roll of elastic film material should be 300 g/2.54 cm or less, preferably 200 g/2.54 cm or less on average and in any event less than the F10 force in the machine direction. Although, generally not needed any anti-blocking agents or release agent modifiers could be added to, or coated on, the invention film or laminate if desired, suitable antiblocking agents would include particulate additives such as calcium carbonate and the like. Release agents would include materials such as silicones, fluoropolymers, stearates et al. Other conventional additives such as dyes, pigments, antioxidants, antistatic agents, bonding aides, heat stabilizers, photo stabilizers, foaming agents, glass bubbles and the like can be used as required in any portion of the incompatible blend.

The invention anisotropic film material can also be the elastic layer in a multilayer film construction such as disclosed in U.S. Pat. Nos. 5,501,675; 5,462,708; 5,354,597 or 5,344,691 the substance of which are substantially incorporated herein by reference. These references teach various forms of multilayer coextruded elastic laminates, with at least one elastic core layer and either one or two relatively inelastic skin layers. The skin layers can be stretched beyond an elastic limit of these layers (i.e., they are permanently deformed) and the coextruded laminate subsequently recovered in the direction opposite to the stretching direction by the relatively higher elastic recovery of the elastic core layer. The result is the formation of a material which is selectively elastic in only those regions which are stretched and recovered.

The skin layers recover little or at least less than the elastic core and are selected so as to form a microtexture or microstructure. Microtexture or microstructure means that the skin layer contains peak and valley irregularities or folds which are large enough to be perceived by the unaided human eye as causing increased opacity over the opacity of a laminate before stretching and recovery. The irregularities are small enough to be perceived as smooth or soft on human skin and magnification is required to see the details of the microtexturing.

The skin layers are generally formed of any semicrystalline or amorphous polymer which is less elastomeric than the elastic core layer and which will undergo relative more permanent deformation than the core layer at the percentage that the elastic laminate is stretched. Slightly elastomeric materials such as olefinic elastomers, e.g., ethylene-propylene elastomers, ethylene propylene diene polymer elastomers, metallocene polyolefin elastomers or ethylene vinyl acetate elastomers can be used as long as the skin layers provided are substantially less elastomeric than the elastic core layer. Preferably, these skin layers are polyolefinic formed predominately of polymers such as polyethylene, polypropylene, polybutylene, polyethylene-polypropylene copolymer, however, these skin layers may also be wholly or partly polyamide, such as nylon, polyester, such as polyethylene terephathalate, or the like, and suitable blends thereof. Generally, the skin layer material following stretching and elastic recovery is in contact with the elastic core layer material in at least one of three suitable modes; first, continuous contact between the elastic core layer and the microtextured skin layer; second, continuous contact between the layers with cohesive failure of the core layer material under the microtextured skin folds; and third, adhesive failure of the skin layer to the core layer under the microtextured folds with intermittent skin layer to core layer contact at the microtexture fold valleys. Generally, in the context of the present invention, all three forms of skin-to-core contact are acceptable. However, preferably the skin and core layers are in substantially continuous contact so as to minimize the possibility of delamination of the skin layer(s) from the elastic core layer.

Generally, the core layer to skin layer thickness ratio will be at least 3, preferably at least 5 but less than 100, and most preferably from 5 to 75. Generally, the overall caliper of the multilayer film is as described above for the anisotropic elastic film material.

The addition of the skin layer materials, as described in the above references, generally tends to further reinforce the anisotropic elastic film material layer in the machine direction. Also following stretching and recovery in the cross direction (CD), the multi-layer film material exhibits substantially identical CD elastic properties to the elastic film core layer itself. As such, the CD stretched and recovered version of this multi-layer film exhibits enhanced anisotropic elastic behavior. However, prior to stretching and recovery the film generally is inelastic in both MD and CD directions.

The anisotropic elastic behavior in these coextruded laminates using the invention anisotropic film layer(s) can be accentuated as described in U.S. Pat. No. 5,462,708 by subjecting a uniaxially stretched laminate to a deactivating heat treatment, while in the stretched condition. The heat treatment is such that the elastic recovery force of the elastic material is allowed to dissipate without substantially affecting the orientation of the inelastic skin materials. The heat treated laminate material is then stretched in a second cross direction and allowed to recover as described above. The resulting material is exceedingly strong in the original stretch direction and elastic in the cross direction. Machine direction orientation can also be used with other embodiments, with or without heat treatment, to provide additional anisotropic behavior to the invention anisotropic film material. This machine direction orientation can be up to the natural draw ratio of the fiber forming polyolefins of the inelastic polymer material portion. Generally this can be an orientation of up to six (6) times the original length of the film, although preferably from 2 to 5 times the original film length.

In an additional embodiment, an extremely thin skin layer can be employed such that the multilayer elastomeric material exhibits substantially complete elastic properties when initially stretched in the CD direction, rather than requiring initial stretch and recovery. The use of such a thin skin layer generally decreases the potential for the anisotropic film to block when formed into a roll, however, generally these skin layers are not required for that purpose. If skin layers are used, the elastic film layer can contain additional materials in the elastomer portion that would increase the film layer's tackiness and as such its tendency to block. Such additives would include diblock copolymers as discussed above, other tack-modifying elastomers such as polyisoprenes, tackifiers, oils, liquid or low molecular weight resins and the like. These tack-modifying materials can assist in the skin layer to core layer adhesion or could be used to modify elastomeric properties, extrusion properties or be used as extenders.

The invention anisotropic elastic film can also be used extensively in laminates with other film layers or nonwoven web materials or other webs such as is known in the art. For example, the anisotropic elastic film can be directly extrusion bonded to a nonwoven material which is extensible in at least the cross direction or alternatively either adhesively or thermally continuously bonded or point bonded to such a web material. Examples of such cross directionally extensible nonwoven web materials include the neckable spunbond, meltblown or bonded carded webs disclosed in U.S. Pat. No. 5,514,470. These neckable nonwoven webs are stretched in the machine direction, for example to 150 percent elongation, such that the nonwoven web substantially and reversibly necks in the cross direction and are then joined to the elastic film layer while so necked. The resulting laminate is generally tensilized in the machine direction while generally elastically extensible in the cross direction. Alternatively, a nonwoven web or film could be corrugated in the cross direction by use of corrugating rolls and subsequently joined to the invention anisotropic elastic film. Certain other nonwoven materials such as some spunlace nonwovens or spunbond nonwovens formed with crimped or crimpable fibers exhibit a natural tendency to elongate in the cross direction.

The invention anisotropic elastic film, whether a single layer film, or a multi-layer film, or a laminate can be used extensively in disposable or limited use garments and the like requiring an elastic exhibiting generally cross directional elasticity. For example, the material can be used extensively as an elastic in a disposable diaper such as waist band elastic, elastic side panels or elastic ear portions or in disposable training pants requiring specific zones of elasticity in order to create a tight-fitting, conformable garment. When used, the invention anisotropic elastic film material would generally be unwound from a roll and cut into suitable sizes and shapes for use in elasticating the disposable garment. The relatively inelastic behavior of the anisotropic film in the machine direction enables the film to be more easily handled and cut into specific forms on conventional film handling machinery without undesirable elongation of the elastic (e.g., causing loss of film tension on the manufacturing line) in the machine direction. The invention material, when cut into appropriate shapes, can be applied in a conventional manner as is known in the art.

The invention material can be formed by conventional film extrusion methods in either the single or multi-layer form in a manner such as described specifically in the examples. The materials are generally fed into one or more rotating screw extruders which feed into a die or feedblock through which a die tip forms the extruded elastic film. If the material is directly extrusion coated onto a nonwoven material the nonwoven is generally brought in less than 2 seconds after the film is extruded from the die tip so as to contact the nonwoven while it is still substantially in a heat softened state.

Test Methods

1. Tear Strength

One end of a specimen approximately 75 mm long and exactly 63 mm wide is positioned in a vertical plane with the long dimension extending horizontally, with the ends of the specimen gripped between a pair of fixed clamps horizontally spaced 2.5 mm from a pair of movable clamps which grip the other end of the test specimen. A 20 mm slit is made in the lower edge of the test specimen between the two pairs of clamps. A pendulum, carrying a circumferential graduated scale, is then allowed to fall freely, tearing the pre-cut test specimen along a continuation of the slit. A frictionally mounted pointer on the scale indicates the resistance in grams of the specimen to tearing. The test is commonly referred to as the Elmendorf tear (ASTM D1922) strength and values are reported in grams per mil (25 microns).

Each of the elastic films of the present invention were measured six times. A normalized value was calculated by dividing the test value by the sample thickness. The normalized values thus obtained were then averaged. Measurements were made in such a manner that the tear in the test specimen was propagated along the machine direction (MD).

2. F10 and F10 Ratio

Strips of elastomeric film measuring 2.54 cm by 15 cm were cut along both the machine direction (MD) and cross direction (CD) of an extruded film sheet.

The F10 force required to stretch each of the samples 10 percent was measured using a standard tensile test configuration as described in ASTM D 882-95a. Each of the measurements was made on three samples. The force obtained was then divided by the sample thickness in mils to give a normalized force value. Each measurement was made three times and the normalized force results were averaged.

The F10 force required for stretching the elastomeric film 10 percent of its original length in the machine direction and the cross direction, respectively, were compared to each other in a ratio and referred to as the F10 Ratio in the data tables in the following examples. The ratio is a dimensionless number.

The F10 force normalized per cross-sectional area (CD) is also reported for the films in the tables.

3. Permanent Set

Specifically, samples of elastomeric film were cut into strips having a width of 2.54 cm and a length of 15 cm.

Elastomeric films of the present invention were stretched to a given percent of their original length and then allowed to recover. This tendency to recover completely or remain partially extended after stretching was determined quantitatively by measuring permanent set in percent. The test was performed using a tensile tester and test sample arrangement as described in ASTM D 882-95a, Tensile Properties of Thin Plastic Sheeting. Elastomeric film samples were extended to 200 percent of their original length, held at that extension for 5 sec, allowed to relax, and measured again after 5 sec. Each elastomeric film was measured three times in the cross direction and the data averaged.

The difference in length before and after extension was divided by the original length and expressed as percent.

Materials

Elastomers

E1 Styrene-isoprene-styrene block copolymer, 15 percent styrene, 83 percent triblock, available as Kraton 1107 from Shell Chemical Co, Houston, Tex.

E2 Styrene-butadiene-styrene block copolymer, 31 percent styrene, available as Kraton 1101 from Shell Chemical Co, Houston, Tex.

E3 Styrene-ethylene/butylene-styrene block copolymer, 13 percent styrene, 65 percent triblock, available as Kraton 1657 from Shell Chemical Co, Houston, Tex.

E4 Styrene-isoprene-styrene block copolymer, 20 percent styrene, 100 percent triblock, available as Vector 4111 from Dexco Polymers, Houston, Tex.

E5 Styrene-isoprene-styrene block copolymer, 29 percent styrene, 100 percent triblock, available as Vector 4211 from Dexco Polymers, Houston, Tex.

Fiber-forming materials

F21 High density polyethylene (HDPE), available as LT6186, 0.96 d, 0.8 MFI, from Quantum Chemicals, Cincinnati, Ohio.

F22 High density polyethylene (HDPE), available as 1288 from Fina Oil and Chemical, Dallas, Tex.

F23 Polypropylene (PP), available as 5A95, MFI 9.5, from Union Carbide, Danbury, Conn.

F24 Polypropylene (PP), available as 5D45, MFI 0.8, from Union Carbide, Danbury, Conn.

F25 Polypropylene (PP), available as Escorene 3085, MFI 35, from Exxon Chemical, Houston , Tex.

F26 Polypropylene (PP), available as Escorene 1012, MFI 5, Exxon Chemical, Houston , Tex.

F27 Polypropylene (PP), available as Dypro 3857, MFI 70, Fina Oil and Chemical, Dallas, Tex.

F29 Polypropylene (PP), available as Dypro 3860, MFI 100, Fina Oil and Chemical, Dallas, Tex.

F30 Polypropylene (PP), available as Escorene 3505, MFI 400, Exxon Chemical, Houston , Tex.

F31 Polypropylene (PP,) available as 442H, 1000 MFI, from Montell North America, Wilmington, Del.

F32 Random copolymer of propylene and ethylene (P-co-E), melt flow index (MFI) 1.5, available as EOD95-08 from Fina Oil and Chemical, Dallas, Tex.

F33 Polypropylene/ethylene-propylene-rubber (PP/EPR), impact block copolymer, MFI 8, available as 7C50 from Union Carbide, Danbury, Conn.

F34 Polystyrene (PS), general purpose crystalline, mfr 4, available as 535BP1 from Fina Oil and Chemical, Dallas, Tex.

F35 Polystyrene (PS), available as G18, MFI 18, from Amoco Polymers, Alpharetta, Ga.

F36 Polypropylene/ethylene-propylene-rubber (PP/EPR), impact block polymer, available as WRD-5-1057, 12 MFI, available from Union Carbide, Danbury, Conn.

F37 Polypropylene (PP), 2.5 MFI, available as 3374 from Fina Oil and Chemical, Dallas, Tex.

F38 Polypropylene (PP), MFI 3.9, available as 5A97 from Union Carbide, Danbury, Conn.

F39 Polypropylene (PP), MFI 12, available as 5-1057 from Union Carbide, Danbury, Conn.

F40 Random copolymer of propylene and ethylene (P-co-E), 3.2 percent ethylene, 1.9 MFI, available as 6D20 from Union Carbide, Danbury, Conn.

Additives/Other

A51 Calcium carbonate ($CaCO_3$), available commercially as G200 $CaCO_3$ with ethylene propylene rubber 80:20, from Omya GmbH, Cologne, Germany.

A52 Processing oil, available as Shellflex 371, from Shell Chemical Co, Houston, Tex.

A53 Polypropylene impact copolymer, available as SRD-7-560, MFI 30, from Union Carbide, Danbury, Conn.

This material was used in multilayer films as a "skin" layer.

General Methods for Film Extrusion

Method 1—Extrusion of single layer films

Single layer films were prepared by extrusion using a single-screw extruder having a screw diameter of 1.9 cm and a length/diameter ratio of 24:1, commercially available from Haake (Paramus, N.J.). The barrel was heated in three zones to temperatures of 163° C., 182° C. and 218° C., respectively, the temperature increasing in the direction of the die.

Materials were compounded by mixing pelletized or crumbed versions of commercially available products and feeding these mixtures by gravity into the extruder. The extruder exit was fitted with a 20 cm wide slot die which was adjusted to extrude film thickness to generally about 100 microns.

The films were formed by casting them into a nip created by a silicone rubber covered roll and a matte finish stainless steel roll, both of which were cooled to approximately 10° C. with chilled water.

The final films were wound into a roll at a speed of about 3 m/min and stored in roll form at approximately 22° C. In cases where it was anticipated that the films might have a tendency to adhere irreversibly to themselves, a silicone-coated paper release liner was wound along with the film into a roll.

The resulting films were untensilized.

All Example and Comparative example films were prepared by this method unless otherwise indicated.

Method 2—Extrusion of multilayer films

A continuous coextrusion was carried out to prepare three-layer laminates with two outer skin layers and a core layer. A 2.5 in (6.3 cm) screw diameter Davis Standard extruder was used to feed the core layer and a 1.5 inch (3.8 cm) screw diameter Davis Standard extruder (available from Davis Standard Corp., Pawcatuck, Conn.) was used to feed the two skin layers into the Cloeren (TM) feedblock. The three layers were extruded through a single manifold 18 inch (46 cm) wide film die. The resulting films were untensilized.

Method 3—Extrusion of Single Layer Films with Orientation

Single layer films were prepared via continuous extrusion using an extruder having a screw diameter of 1.75 in (4.4 cm) and a L/D ratio of 24:1. Four extruder barrel zones were heated to 171° C., 193° C., 204° C. and 216° C., respectively and the slot die to 216° C. Films were formed by casting into a nip formed by a silicone rubber covered roll and a matte finish metal roll, both of which were water-cooled to 10° C. Films were then wound into a roll.

In a subsequent step, the film was oriented in the machine direction by first preheating the film to 104° C. and then stretching the softened film between two nips, where the second nip was running at a higher speed than the first nip.

EXAMPLES

Comparative Example 1 and Example 1

Comparative Example 1 was prepared by extruding a single layer of styrene-isoprene-styrene synthetic rubber, denoted as E1 (styrene-isoprene-styrene block copolymer, 15 percent styrene, 83 percent triblock, available as Kraton 1107 from Shell Chemical Co, Houston, Tex.), using the technique described under Method 1.

Example 1 was prepared in the same manner as Comparative Example 1, except that 50 parts high density polyethylene (HDPE) was added to 50 parts of the styrene-isoprene-styrene base elastomer as it was fed into the extruder. The high density polyethylene (HDPE), denoted as F21, is available as LT6186, 0.96 d, 0.8 MFI, from Quantum Chemicals, Cincinnati, Ohio.

Chemical composition of the films of the examples is expressed in per cent by weight unless otherwise noted.

Extruded films were evaluated by the methods described under Test Methods above: F10 Ratio (ratio of force required to stretch the film 10 percent in the machine direction vs. the cross direction), permanent set after elongation to 200 percent and Elmendorf tear. Test results are also recorded in Table 1.

Comparative Example 2 and Examples 2 through 4

A second Comparative Example was prepared in a fashion identical with Comparative Example 1, with the exception that a different styrene-isoprene-styrene elastomer was employed. The elastomer used in this example, denoted as E4 in the Tables, was 20 percent styrene, 80 percent isoprene and 100 percent ABA triblock, available as Vector 4111 from Dexco Polymers, Houston, Tex.

Examples 2 through 4, respectively, were prepared using Method 1 by adding high density polyethylene (HDPE) of the amounts and kind described in Table 1 to the base elastomer E4. Samples were tested as in the previous examples and the results recorded in Table 1.

TABLE 1

| | | | Test Results | | | |
|---|---|---|---|---|---|---|
| Ex. | Elastomer Kind, % | Fiber Kind, % | F10 Ratio | Perm. set (CD), % | Tear, g/25μ | F10 (CD) kg/cm² |
| C1 | E1, 100 | None | 1.04 | 12.7 | 14 | 1.1 |
| 1 | E1, 50 | F21, 50 | 3.25 | 32.9 | 56 | 8.1 |
| C2 | E4, 100 | None | 1.00 | 0.1 | 13 | 2.1 |
| 2 | E4, 40 | F22, 60 | 1.98 | 40.9 | 47 | 27.5 |
| 3 | E4, 40 | F21, 60 | 2.60 | 47.4 | 54 | 35.8 |
| 4 | E4, 70 | F22, 30 | 1.08 | 15.9 | — | 2.8 |

The addition of HDPE to SIS elastomer produced anisotropic elastic films which films also exhibited substantially improved tear resistance in the machine direction.

Examples 5 through 17

Examples 5 through 17 were also prepared by the general method (Method 1) for extruding single layer films, again using styrene-isoprene-styrene block polymers denoted as E1 and E4 as elastomeric bases. In this set of examples, however, several polypropylenes having various melt indices, were used a fiber-forming additives. In Examples 6 and 9, respectively, an ethylene-propylene copolymer, denoted as F32, was employed and in Example 15, a high density polyethylene (HDPE), denoted as F21, was added.

This set of examples was run under very similar conditions within a period of several consecutive hours.

Material compositions and test results are summarized in Table 2.

TABLE 2

| | Elastomer (SIS) | | Fiber | | F10 | Test Results | | |
|---|---|---|---|---|---|---|---|---|
| | | | | | | Permanent set (CD), | Tear (MD), | F10 (CD) |
| Ex. | Kind, % | Type | Kind, % | Ratio | | % | g/25μ | kg/cm² |
| 5 | E1, 60 | PP | F23, 40 | 6.79 | | 25.3 | 47 | 7.7 |
| 6 | E1, 60 | P-co-E | F32, 40 | 4.97 | | 20.0 | 42 | 2.1 |
| 7 | E1, 60 | PP | F24, 40 | 1.80 | | 22.5 | 50 | 3.7 |
| 8 | E4, 60 | PP | F23, 40 | 6.72 | | 18.7 | 28 | 4.3 |
| 9 | E4, 60 | P-co-E | F32, 40 | 2.70 | | 14.7 | 33 | 3.5 |
| 10 | E4, 60 | PP | F24, 40 | 2.84 | | 16.7 | 29 | 3.6 |
| 11 | E4, 60 | PP | F37, 40 | 3.22 | | 14.4 | 32 | 3.2 |
| 12 | E4, 60 | PP | F38, 40 | 5.71 | | 13.5 | 23 | 3.1 |
| 13 | E1, 60 | PP | F37, 40 | 4.29 | | 14.7 | 34 | 3.5 |
| 14 | E1, 60 | PP | F38, 40 | 7.68 | | 22.1 | 31 | 4.9 |
| 15 | E4, 60 | HDPE | F21, 40 | 4.35 | | 19.8 | 32 | 2.4 |
| 16 | E4, 60 | PP | F39, 40 | 6.30 | | 13.1 | 20 | 3.6 |
| 17 | E4, 60 | P-co-E | F40, 40 | 2.70 | | 14.4 | 25 | 3.5 |

All the elastomer films in these examples exhibited anisotropic behavior and tear resistance values higher than the base elastomer alone. The extremely low MFI polypropylene, less than 1, did not provide as much anisotropic behavior as the higher MFI polypropylenes (greater than 2.0).

Examples 18 through 28

Elastomeric films of the invention were prepared in Examples 18 through 26 by extruding styrene-isoprene-styrene block copolymer elastomer in combination with a series of polypropylenes having a wide range of melt flow indices.

A further Example 27 was prepared using a random copolymer of ethylene and propylene, available commercially as EOD95-08 from Fina Oil & Chemical.

Another Example 28 was prepared using an impact copolymer available as 7C50 from Union Carbide.

Comparative Examples 1 and 2 are included in Table 3 for reference. Compositions of the materials and test results are shown in Table 3.

TABLE 3

| | Elastomer | Fiber | | F10 | Test Results Perm. set (CD), | Tear, | F10 (CD) |
|---|---|---|---|---|---|---|---|
| Ex. | Kind, % | Type | Kind, % | Ratio | % | g/25µ | kg/cm² |
| C1 | E1, 100 | None | None | 1.04 | 12.7 | 14 | 1.1 |
| 18 | E1, 60 | PP | F23, 40 | 4.77 | 38.8 | 63 | 16.5 |
| 19 | E1, 60 | PP | F24, 40 | 3.76 | 19.2 | 62 | 2.7 |
| 20 | E1, 60 | PP | F25, 40 | 8.68 | 25.4 | 103 | 3.9 |
| C2 | E4, 100 | None | None | 1.00 | 0.1 | 13 | 2.1 |
| 21 | E4, 60 | PP | F26, 40 | 7.04 | 23.2 | 36 | 6.4 |
| 22 | E4, 60 | PP | F23, 40 | 6.40 | 18.3 | 30 | 8.9 |
| 23 | E4, 60 | PP | F27, 40 | 2.80 | 28.1 | 68 | 20.3 |
| 24 | E4, 60 | PP | F29, 40 | 3.43 | 23.1 | 56 | 14.5 |
| 25 | E4, 60 | PP | F30, 40 | 2.54 | 47.3 | 60 | 32.4 |
| 26 | E4, 60 | PP | F31, 40 | 3.18 | 48.7 | 51 | 29.2 |
| 27 | E4, 60 | P-co-E | F32, 40 | 1.93 | 33.1 | 16 | 4.1 |
| 28 | E4, 50 | PP/EPR | F33, 50 | 3.71 | 36.4 | 89 | 21.9 |

Generally all the polypropylenes worked but those in a preferred MFI range of from about 2.5 to 40 exhibited the best combination of anisotropic behavior and tear resistance.

Examples 29 through 30

Elastomeric films of the invention were prepared using two differing types of block polymers in combination with a single polypropylene as a fiber-forming material. Example 29 was prepared using the styrene-isoprene-styrene block polymer denoted as E1. Example 30 was prepared in an identical fashion to Example 29, with the exception that a styrene-butadiene-styrene block polymer was employed as a base elastomer material.

The compositions of the films and test results are summarized in Table 4.

TABLE 4

| | Elastomer | Fiber | F10 | Test Results Permanent | Tear, | F10 (CD) |
|---|---|---|---|---|---|---|
| Ex. | Type | Kind, % | Kind, % Ratio | set, % | g/25µ | kg/cm² |
| 29 | S-I-S | E1, 60 | F23, 40 | 3.41 | 42.0 | 47 | 7.8 |
| 30 | S-B-S | E2, 60 | F23, 40 | 1.88 | 56.5 | 181 | 54.3 |

Examples 31 through 32

Elastomeric films of the invention were prepared by adding a random copolymer of propylene and ethylene (P-co-E) to two differing block polymers.

Example 31 employs a styrene-isoprene-styrene block polymer, denoted as E1.

Example 32 employs the same fiber-forming ethylene-propylene copolymer in the same amount as in Example 31, but in combination with a different elastomer, a styrene-ethylene butylene-styrene block copolymer, denoted as E3.

Film compositions and test results are summarized in Table 5.

TABLE 5

| | Elastomer | Fiber | F10 | Test Results Perm. set, | Tear, | F10 (CD) |
|---|---|---|---|---|---|---|
| Ex. | Type | Kind, % | Kind, % | Ratio | % | g/25µ | kg/cm² |
| 31 | S-I-S | E1, 45 | F32, 55 | 4.49 | 40.7 | 95 | 11.0 |
| 32 | S-EB-S | E3, 45 | F32, 55 | 2.13 | 74.7 | 187 | 22.7 |

Example 33

Example 33 was prepared by combining an S-I-S block polymer, denoted as E5 (60 parts), polypropylene denoted as F23 (35 parts) and processing oil denoted as A52 (5 parts), commercially available as Shellflex 371 from Shell Chemical, Houston, Tex.

Test measurements showed the F10 Ratio as 5.47, a tear of 81 g/25 µ and a permanent set in percent of 20.9.

Examples 34 through 36

Elastic films of the present invention were extruded using Method 1 except that calcium carbonate, commercially available as Omylene G200 from Omya, was added to the polymer mixtures of Examples 35 and 36 as they were fed into the extruder. Examples 34 contains no calcium carbonate.

Chemical composition of the films as well as test results are summarized in Table 6.

TABLE 6

| | Elastomers (SIS) | Fiber (PP) | CaCO₃, | F10 | Test Results Perm. set (CD), | Tear, | Unwind, g/2.54 | F10 (CD) |
|---|---|---|---|---|---|---|---|---|
| Ex. | Kind, % | Kind, % | % | Ratio | % | g/25µ | cm | kg/cm² |
| 34 | E4, 65 | F23, 35 | 0 | 5.50 | 26.2 | 30 | 227 | 8.6 |
| 35 | E4, 61 | F23, 35 | 4 | 5.05 | 24.7 | 45 | 90 | 11.1 |
| 36 | E4, 57 | F23, 35 | 8 | 5.50 | 30.3 | 57 | 28 | 9.5 |

All the films could be unwound but the addition of calcium carbonate dramatically decreased the force needed to unwind the films.

Comparative Examples 3 through 6

Comparative Examples 3 through 6 were prepared to demonstrate the effects of using polystyrene as a fiber-forming material as disclosed in Japanese Application Kokai No. 5-186611.

Comparative Examples 1 and 2, described previously, showing base elastomer materials having no fiber-forming polymer material, are included in Table 7 for comparative purposes.

Film compositions and test results are summarized in Table 7.

TABLE 7

| Ex. | Elastomer (SIS) Kind, % | Fiber (PS) Kind, % | F10, Ratio | Test Results Perm. set (CD), % | Tear, g/25μ | Unwind, g/2.54 cm | F10 (CD) kg/cm² |
|---|---|---|---|---|---|---|---|
| C2 | E4, 100 | — | 1.0 | 0.1 | 13 | * | 2.1 |
| C3 | E4, 90 | F34, 10 | 5.53 | 0 | 17 | * | 1.4 |
| C4 | E4, 80 | F34, 20 | 11.49 | 0 | — | * | 1.8 |
| C5 | E4, 70 | F34, 30 | 5.40 | 13.8 | 6 | * | 6.7 |
| C1 | E1, 100 | — | 1.04 | 12.7 | 14 | * | 1.1 |
| C6 | E1, 70 | F34, 30 | 10.27 | 7.2 | 11 | 333 | 5.5 |

*Adjacent layers in roll were adhered permanently to one another. No unwind value could be measured.

Although these films (C3–C6) exhibited very good anisotropic elastic qualities the tear resistance was poor and the films could not be unwound or unwound with great difficulty.

Comparative Examples 7 through 12

These Comparative examples were prepared as with Comparative examples 3 through 5 above. The C7 film of the base elastomer material alone was prepared on the same day with the same lot of polymer to ensure internal consistency of the test results.

Film compositions and test results are summarized in Table 8.

TABLE 8

| Ex. | Elastomer Kind, % | Fiber Type | Fiber Kind, % | F10 Ratio | Test Results Perm. set, % | Tear, g/25μ | F10 (CD) kg/cm² |
|---|---|---|---|---|---|---|---|
| C7 | E4, 100 | — | — | 0.92 | 0.1 | 27 | 1.9 |
| C8 | E4, 90 | PS | E34, 10 | 2.05 | 0.0 | 18 | 3.4 |
| C9 | E4, 80 | PS | E34, 20 | 2.91 | 0.0 | 10 | 6.1 |
| C10 | E4, 70 | PS | E34, 30 | 5.70 | 14.6 | 6.8 | 11.8 |
| C11 | E4, 60 | PS | E34, 40 | 4.60 | 19.7 | 7.6 | 15.9 |
| C12 | E4, 50 | PS | E34, 50 | 4.32 | 30.5 | 5.5 | 30.5 |

These films were not tested for unwind but generally they were quite tacky and not likely unwindable. The tear results were uniformly poor decreasing with the increasing addition of polystyrene.

Examples 37 through 40 and Comparative Example 13

Examples 37 through 40 were prepared using the coextrusion technique described above in Method 2 of the General Methods.

Examples 37 through 40 consist of 1) a central core comprising an elastomer and fiber-forming materials and 2) two thinner skin layers, one on either side of the thicker core, resulting in a skin-core-skin three-layer construction. Skin layers comprise the polymer denoted as A53, polypropylene impact polymer, available as SRD-7-560, MFI 30, from Union Carbide, Danbury, Conn.

A comparative example having skins, but no fiber-forming polymer in the core, is included as Comparative Example 13.

Composition as well as test results are summarized in Table 9.

TABLE 9

| | Core | Fiber | | Skin Thickness, μ | | Test Results | Tear | |
|---|---|---|---|---|---|---|---|---|
| Ex. | Elastomer Kind, % | Kind, % | Thick., μ | Kind | ness, μ | F10 Ratio | Perm. set, % | (MD), g/25μ | F10 (CD) kg/cm² |
| C13 | E1, 100 | None | 100 | A53 | 2.5 | 1.95 | 24.7 | — | 2.4 |
| 37 | E1, 80 | F39, 20 | 100 | A53 | 2.5 | 3.37 | 18.9 | 33 | 5.2 |
| 38 | E1, 70 | F39, 30 | 100 | A53 | 2.5 | 4.59 | 21.1 | 16 | 6.5 |
| 39 | E1, 60 | F39, 40 | 100 | A53 | 2.5 | 5.10 | 27.6 | 25 | 9.8 |
| 40 | E1, 50 | F39, 50 | 100 | A53 | 2.5 | 2.44 | 60.0 | 57 | 27.6 |

The skin layers themselves are somewhat oriented in the extrusion process and as such create anisotropic behavior in the C13 film. The addition of polypropylene to the core layer further increased anisotropic behavior.

Examples 41 through 47 and Comparative Examples 14 and 15

A series of examples was prepared where the amount of the fiber-forming material was varied in a broad range of from 0 percent to 100 percent.

Comparative Example 2, described previously and representing the base elastomer with no fiber-forming material, is again included for comparative purposes.

Comparative Example 15 represents pure polypropylene and no elastomer base material.

Examples 41 through 47 show a styrene-isoprene-styrene base elastomer, denoted as E4, in combinations with polypropylene (PP), denoted as F23, in amounts ranging from 20 percent to 60 percent, with Comparative example 14 having 75 percent polypropylene.

Compositions of the materials as well as corresponding test results are shown in Table 10.

TABLE 10

| Ex. | Elastomer (SIS) Kind, % | Fiber Kind, % | F10, Ratio | Test Results Perm. set (CD), % | Tear (MD), g/25µ | F10 (CD) kg/cm² |
|---|---|---|---|---|---|---|
| C2 | E4, 100 | — | 1.00 | 0.1 | 13 | 2.1 |
| 41 | E4, 80 | F23, 20 | 3.02 | 18.5 | 14 | 4.4 |
| 42 | E4, 70 | F23, 30 | 4.51 | 20.4 | 13 | 4.5 |
| 43 | E4, 65 | F23, 35 | 3.87 | 24.1 | 13 | 6.2 |
| 44 | E4, 60 | F23, 40 | 3.30 | 38.2 | 63 | 20.3 |
| 45 | E4, 50 | F23, 50 | 3.12 | 45.3 | 72 | 25.0 |
| 46 | E4, 45 | F23, 55 | 2.31 | 57.1 | 68 | 37.2 |
| 47 | E4, 40 | F23, 60 | 1.83 | 80.8 | 119 | 62.0 |
| C14 | E4, 25 | F23, 75 | 1.27 | >100 | 184 | 146.1 |
| C15 | — | F23, 100 | 1.02 | >100 | 62 | 229.6 |

The improvements in tear resistance didn't occur, with this particular combination of elastomer and polypropylene, until after 35 percent polypropylene was added. Although tear resistance was improved with respect to this combination of materials at 35 percent polypropylene in Example 34. This variability was often noted and is likely due to slight variations in process conditions such as mixing, extrusion conditions or the like or polymer lot variability. However, generally the same trends are noted with any given selection of materials processed under identical conditions in terms of properties such as tear resistance and anisotropic elastic behavior. Generally the addition of a polyolefin did not negatively effect tear (whereas polystyrene did generally negatively effect tear resistance) and at some level improved tear resistance. The addition of polyolefins also generally resulted in a peak anisotropic behavior at some level (generally from 30 to 50 percent polyolefin) with decreases on either side of the peak value. The amount of permanent set also increased generally linearly with the addition of polyolefins until it became unacceptable (generally at a ratio of from 0.4:1 to 0.6:1 elastomer portion to polyolefin portions).

Examples 48 through 51

Examples 48 through 51 were prepared using an identical polymer composition, comprising 50 percent styrene-isoprene-styrene block copolymer (E4) as the base elastomer, and 50 percent by weight random copolymer of propylene and ethylene (P-co-E) (F32).

Example 48 represents the extruded elastomeric film in an unoriented state.

In Examples 49 through 51, the extruded polymeric films were drawn in the machine directions according to Method 3 in the amounts of 1.5-fold, 2-fold and 2.5-fold, respectively.

Film composition and test results are summarized in Table 11.

TABLE 11

| Ex. | Elastomer Kind, % | Fiber Kind, % | Draw Machine direct | Test Results F10, MD/CD | Perm. set (CD), % | Tear (MD), g/25µ | F10 (CD) kg/cm² |
|---|---|---|---|---|---|---|---|
| 48 | E4, 50 | F32, 50 | 0 | 2.4 | 42.5 | 90 | 20.1 |
| 49 | E4, 50 | F32, 50 | 1.5 | 3.59 | 35.7 | 56 | 21.9 |
| 50 | E4, 50 | F32, 50 | 2.0 | 4.90 | 32.8 | 99 | 19.2 |
| 51 | E4, 50 | F32, 50 | 2.5 | 5.97 | 27.2 | 64 | 20.0 |

The post extrusion orientation improved the anisotropic elastic properties of the films. Generally, tear resistance was not significantly effected by the machine direction orientation.

We claim:

1. An anisotropic elastic extruded film comprising an anisotropic elastic film sheet material having a machine direction and a cross direction and having a thickness of from 20 to 300 microns formed of an extruded blend of a block copolymer elastomer portion and a polyolefin polymer portion blended in a ratio of from 10:1 to 0.4:1, respectively, the elastomer portion comprised of block copolymer elastomer formed of A blocks and B blocks, the A blocks are formed predominantly of monoalkyenyl arene and the B blocks are formed predominately of conjugated diene and the polyolefin portion is comprised predominately of an inelastic fiber forming polyolefin polymer, copolymer or blend, wherein the anisotropic film layer has a F10 force (as measured by ASTM D882-95a) ratio, which F10 ratio is of the machine direction (MD) F10 force to the cross direction (CD) F10 force, of at least 1.5.

2. The anisotropic elastic film sheet material of claim 1 comprising a roll of monolayer film.

3. The anisotropic elastic film sheet material of claim 2 wherein the roll of film has an unwind force of less than 300 g/2.54 cm.

4. The anisotropic elastic film sheet material of claim 2 wherein the F10 force in the machine direction is greater than the unwind force.

5. The anisotropic elastic film sheet material of claim 1 wherein the film comprises a multilayer film of said anisotropic elastic film as a first layer and at least one other polymer film layer.

6. The anisotropic elastic film sheet material of claim S wherein said at least one other polymer film layer is a relatively inelastic film layer compared to said anisotropic film sheet material first layer.

7. The anisotropic elastic film sheet material of claim 6 wherein said at least one other polymer film layer is a polyolefin film layer.

8. The anisotropic elastic film sheet material of claim 6 wherein said at least one other polymer film layer comprises two such film layers one on either face of said anisotropic elastic film sheet material first layer.

9. The anisotropic elastic film sheet material of claim 6 wherein said film layers are coextruded.

10. The anisotropic elastic film sheet material of claim 1 wherein said monoalkenyl arene is a styrene monomer and said conjugated diene comprises 1,3-butadiene, isoprene or ethylene-butylene.

11. The anisotropic elastic film sheet material of claim 10 wherein said conjugated diene is isoprene.

12. The anisotropic elastic film sheet material of claim 11 wherein said polyolefin portion is a polypropylene polymer, copolymer or blend.

13. The anisotropic elastic film sheet material of claim 12 wherein said elastomer portion to polyolefin portion ratio is from 5:1 to 0.6:1.

14. The anisotropic elastic film sheet material of claim 13 wherein said block copolymer elastomer portion is predominately multi-block block copolymer.

15. The anisotropic elastic film sheet material of claim 14 wherein said multi-block copolymer is an ABA triblock copolymer.

16. The anisotropic elastic film sheet material of claim 14 wherein said multi-block copolymer comprises 50 to 100 weight percent of the block copolymer of the elastomer portion.

17. The anisotropic elastic film sheet material of claim 16 wherein said elastomer portion block copolymer further comprises 0 to 50 weight percent AB diblock copolymer.

18. The anisotropic elastic film sheet material of claim 1 wherein said anisotropic elastic film sheet material has an average tear strength of at least 20 g/25 $\mu$.

19. The anisotropic elastic film sheet material of claim 1 wherein said anisotropic elastic film sheet material has an average tear strength of at least 30 g/25 $\mu$.

20. The anisotropic elastic film sheet material of claim 1 wherein said anisotropic elastic film sheet material comprises a laminate of said anisotropic elastic film sheet material and at least a second web which is extensible in at least the cross direction of the anisotropic elastic film layer to which the second web is attached.

21. The anisotropic elastic film sheet material of claim 20 wherein said second web is a nonwoven fibrous web.

22. The anisotropic elastic film sheet material of claim 16 wherein said FIO Ratio is greater than 2.0.

23. The anisotropic elastic film sheet material of claim 1 wherein the permanent set of the anisotropic elastic film sheet material in the CD direction is less than 80 percent when the film layer is stretched by 200 percent.

24. The anisotropic elastic film sheet material of claim 15 wherein the permanent set of the anisotropic elastic film sheet material in the CD direction is less than 50 percent when the film layer is stretched by 200 percent.

25. The anisotropic elastic film sheet material of claim 1 wherein the anisotropic elastic film sheet material is oriented in the machine direction up to the natural draw ratio of the fiber forming polyolefin.

26. The anisotropic elastic film sheet material of claim 1 wherein the anisotropic elastic film sheet material has a F10 force in the cross direction of less than about 60 kg/cm$^2$.

27. The anisotropic elastic film sheet material of claim 1 wherein the anisotropic elastic film sheet material has a F10 force in the cross direction of less than about 40 kg/cm$^2$.

28. The anisotropic elastic film sheet material of claim 1 wherein the anisotropic elastic film sheet material has a F10 force in the cross direction of less than about 20 kg/cm$^2$.

* * * * *